(12) United States Patent
Groszmann et al.

(10) Patent No.: US 10,398,393 B2
(45) Date of Patent: *Sep. 3, 2019

(54) DYNAMIC REFERENCE METHOD AND SYSTEM FOR INTERVENTIONAL PROCEDURES

(71) Applicant: Stryker European Holdings I, LLC, Kalamazoo, MI (US)

(72) Inventors: Daniel Eduardo Groszmann, Cambridge, MA (US); Michel Francois Grimaud, Montrouge (FR); Yves Lucien Trousset, Palaiseau (FR)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 1460 days.

This patent is subject to a terminal disclaimer.

(21) Appl. No.: 13/681,916

(22) Filed: Nov. 20, 2012

(65) Prior Publication Data
US 2013/0079628 A1 Mar. 28, 2013

Related U.S. Application Data

(63) Continuation-in-part of application No. 11/906,445, filed on Oct. 2, 2007, now Pat. No. 8,315,690.

(51) Int. Cl.
*A61B 6/12* (2006.01)
*A61M 25/01* (2006.01)
(Continued)

(52) U.S. Cl.
CPC .............. *A61B 6/12* (2013.01); *A61B 6/5217* (2013.01); *A61B 34/20* (2016.02);
(Continued)

(58) Field of Classification Search
CPC ...... A61B 2034/2051; A61B 2090/364; A61B 2090/376; A61B 34/20; A61B 6/02;
(Continued)

(56) References Cited

U.S. PATENT DOCUMENTS 4,869,247 A 9/1989 Howard et al.
5,125,888 A 6/1992 Howard et al.
(Continued)

FOREIGN PATENT DOCUMENTS

WO 2007113719 10/2007

OTHER PUBLICATIONS

Aron, Michael; Coupling electromagnetic sensors and ultrasound images for tongue tracking: acquisition set up and preliminary results; 7th International Seminar on Speech Production—OSSP'06 (2006) [inria—001106304—Version 1].

*Primary Examiner* — Michael T Rozanski
(74) *Attorney, Agent, or Firm* — Howard & Howard Attorneys PLLC

(57) ABSTRACT

An interventional device configured for placement in or near an internal organ or tissue is provided. The interventional device includes a reference portion having three or more sensor elements. In one implementation, the interventional device and associated sensor elements provide dynamic referencing of the internal organ, tissue or associated vasculature after registration of the sensor data with images and/or volumetric representations of the internal organ or tissue.

11 Claims, 8 Drawing Sheets

(51) Int. Cl.
*A61B 6/00* (2006.01)
*A61B 34/20* (2016.01)
*A61B 6/02* (2006.01)
*A61B 8/08* (2006.01)
*A61B 90/00* (2016.01)

(52) U.S. Cl.
CPC .... *A61M 25/0108* (2013.01); *A61M 25/0127* (2013.01); *A61B 6/02* (2013.01); *A61B 8/0833* (2013.01); *A61B 2034/2051* (2016.02); *A61B 2090/364* (2016.02); *A61B 2090/376* (2016.02)

(58) Field of Classification Search
CPC ....... A61B 6/12; A61B 6/5217; A61B 8/0833; A61M 25/0108; A61M 25/0127
USPC .......................................................... 600/424
See application file for complete search history.

(56) References Cited

U.S. PATENT DOCUMENTS

| | | | |
|---|---|---|---|
| 5,211,165 A | 5/1993 | Dumoulin et al. | |
| 5,654,864 A | 8/1997 | Ritter et al. | |
| 5,707,335 A | 1/1998 | Howard et al. | |
| 5,769,843 A * | 6/1998 | Abela | A61B 5/06 600/424 |
| 5,779,694 A | 7/1998 | Howard et al. | |
| 6,675,037 B1 | 1/2004 | Tsekos | |
| 6,783,536 B2 | 8/2004 | Vilsmeier et al. | |
| 6,947,788 B2 | 9/2005 | Gilboa et al. | |
| 6,973,339 B2 | 12/2005 | Govari | |
| 7,850,685 B2 | 12/2010 | Kunis et al. | |
| 8,060,184 B2 | 11/2011 | Hastings et al. | |
| 2003/0220557 A1 | 11/2003 | Clean et al. | |
| 2004/0097804 A1* | 5/2004 | Sobe | A61B 17/3207 600/424 |
| 2005/0084147 A1 | 4/2005 | Groszmann | |
| 2005/0107687 A1 | 5/2005 | Anderson | |
| 2005/0169510 A1 | 8/2005 | Zuhars et al. | |
| 2006/0039591 A1 | 2/2006 | Zettel et al. | |
| 2008/0079421 A1 | 4/2008 | Jensen | |
| 2011/0054293 A1* | 3/2011 | Markowitz | G01S 5/0263 600/407 |
| 2012/0289823 A1* | 11/2012 | Lee, II | A61N 1/025 600/424 |

* cited by examiner

DYNAMIC REFERENCE METHOD AND SYSTEM FOR INTERVENTIONAL PROCEDURES

CROSS-REFERENCE TO RELATED APPLICATIONS

This application is a continuation-in-part application of U.S. patent application Ser. No. 11/906,445, entitled "Dynamic Reference Method and System for Interventional Procedures," filed Oct. 2, 2007, which is herein incorporated by reference in its entirety for all purposes.

BACKGROUND

The present technique relates generally to interventional procedures, such as interventional medical procedures. In particular, the present technique relates to image-guided interventional techniques, such as those used in conjunction with various radiology procedures.

As medical imaging technologies have matured, it has become possible to combine the use of medical imaging techniques with the performance of invasive procedures. For example, interventional procedures such as biopsies and tumor ablations may benefit from the use of imaging techniques that allow a clinician to visualize the target region along with the intervention device while the procedure is being performed. In this way, the clinician may guide the interventional device to the target region with relative accuracy and, perhaps, without unnecessary tissue damage.

In practice, such image-guided interventional techniques typically employ a tracking frame of reference device placed proximate to the anatomy of interest. The reference device moves with the patient to provide accurate and consistent tracking of the anatomy of interest. Typically, the reference device needs to be rigidly secured to the anatomy of interest. As a result, the reference device is generally attached to hard bone near the anatomy of interest. As a result, such image-guided interventional techniques are generally limited to regions in the body bounded by bony anatomy, such as cranial neurosurgery, spine, orthopedic, and sinus procedures.

While such techniques are useful, clearly there are other areas of the body that are not bounded by bony structures and that might also benefit from such image-guided techniques. However, regions of the body that are not bounded by such bony structures, such as cardiac and abdominal regions, currently cannot benefit from such image-guided techniques due to the inability to affix a reference device proximate to the anatomy of interest. Further, many internal organs that might benefit from image-guided interventional techniques can move, such as due to respiration, gravity, and so forth, and therefore, present additional interventional challenges. In addition, even in regions of the anatomy where there is proximate bone, it may not be desirable to attach a reference device to the bone. Therefore, it is desirable to provide a reference technique for image-guided interventional procedures that does not require a reference device affixed to skeletal structures.

BRIEF DESCRIPTION

The present technique is generally directed to the dynamic referencing of an internal structure in an image-guide interventional procedure. In one implementation, an interventional device having three or more sensor elements is provided. In such an embodiment, the interventional device is placed on or in an internal structure, such as an internal organ or vasculature, such as during an interventional procedure. Signals or fields generated by the sensor elements, such as electromagnetic signals or fields, may be used to determine the positions of the sensor elements. The positions of the sensor elements may then be registered with a set of image based data which may or may not include image data representative of the sensor elements. In one embodiment, the registration occurs automatically. Once the signals generated by the sensor elements is registered with the images or volumetric representations of the internal structure, the position and orientation information derived from the sensor elements may be used to modify or adjust the visual representation of the internal structure to reflect motion or deformation of the structure. The modified or adjusted visual representation may then be used to allow a surgeon or other clinician to perform an image-guided invasive procedure based on images reflecting the current position and shape of the internal structure.

In accordance with one aspect of the present technique, a tracking system is provided. The tracking system includes an interventional device. The interventional device includes a reference portion configured for placement proximate to or inside an internal organ. The reference portion is not physically attached to the internal organ when so placed. The interventional device also includes two or more sensor elements integrated on the reference portion. Each sensor element is configured to provide at least position information. Additionally, each sensor element is sized differently or positioned so as to be identifiable in a radiographic image. The tracking system also includes a controller configured to receive the position information generated by the two or more sensor elements. The controller is also configured to register the two or more sensor elements to the corresponding position information in the radiographic image of the internal organ based at least in part upon the size or position differences between the two or more sensor elements.

In accordance with a further aspect of the present technique, a tracking system is provided. The tracking system includes an interventional device. The interventional device includes a reference portion configured for placement proximate to or inside an internal organ. The reference portion is not physically attached to the internal organ when so placed. The interventional device also includes one or more magnetoresistance sensors integrated with the reference portion. The one or more magnetoresistance sensors generate at least position information in response to an externally generated magnetic field. The tracking system also includes a controller configured to receive the position information generated by the one or more magnetoresistance sensors. The controller is also configured to register the one or more magnetoresistance sensors to the corresponding position information in a radiographic image.

In accordance with an additional aspect of the present technique, a tracking system is provided. The tracking system includes an interventional device. The interventional device includes a reference portion configured for placement proximate to or inside an internal organ. The reference portion is not physically attached to the internal organ when so placed. The interventional device also includes one or more magnetoresistance sensors integrated on the reference portion. The one or more magnetoresistance sensors are configured to generate a first set of position data in response to an applied magnetic field. The tracking system also a surgical tool including one or more additional magnetoresistance sensors integrated on the surgical tool. The one or more additional magnetoresistance sensors are configured to generate a second set of position data in response to the applied magnetic field. Additionally, the tracking system includes a controller configured to receive the first and the second set of position data. The controller is also configured to register the first and the second set of position data with a radiographic image of the internal organ.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The present technique is directed to dynamic referencing of internal organs for image-guided interventional procedures. In particular, the present technique utilizes an interventional device configured with one or more tracking devices. The interventional device is configured for placement next to or in an internal organ of interest such that movement of the organ can be tracked in conjunction with acquired images or image data. In particular, in an embodiment, the movement of the tracking devices is automatically registered with the image data, without the use of anatomical or fiducial markers. In this manner, an image-guided interventional procedure may be performed using the dynamic reference information acquired using the interventional device. Because the interventional device can be associated with the anatomy of interest without being affixed to bone, the present technique may be suitable for use with percutaneous procedures performed on internal organs that may move or be moved and which are not close to a suitable skeletal anchor. Examples of such organs include, but are not limited to the liver, lungs, kidneys, pancreas, bladder, and so forth.

Figure 1:
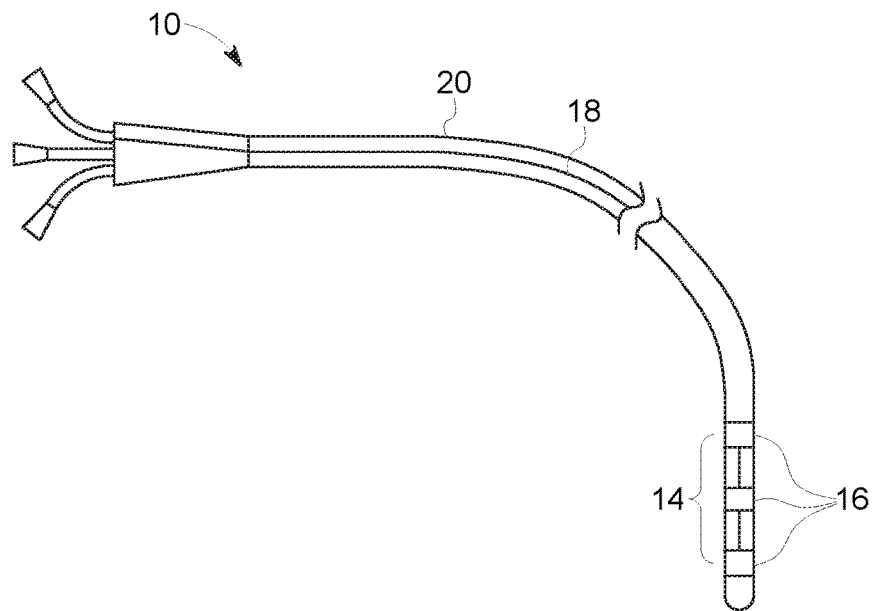
FIG. 1 depicts an interventional device including sensor components, in accordance with an embodiment of the present technique.

For example, referring to FIG. 1, an interventional device 10 is depicted that is suitable for placement near, in, or on an organ of interest. The interventional device 10 includes a reference portion 14. The reference portion 14 includes, in this example, three or more sensor elements 16 that, in one embodiment, may be used to acquire position information relating to the reference portion 14. In other examples, depending on the type of sensor elements 16 employed, fewer sensor elements (i.e., one or two) may be employed. In the depicted embodiment, a conductive element 18 is also provided which may be suitable for providing power to the sensor elements 16 in implementations in which the sensor elements are powered.

Figure 2:
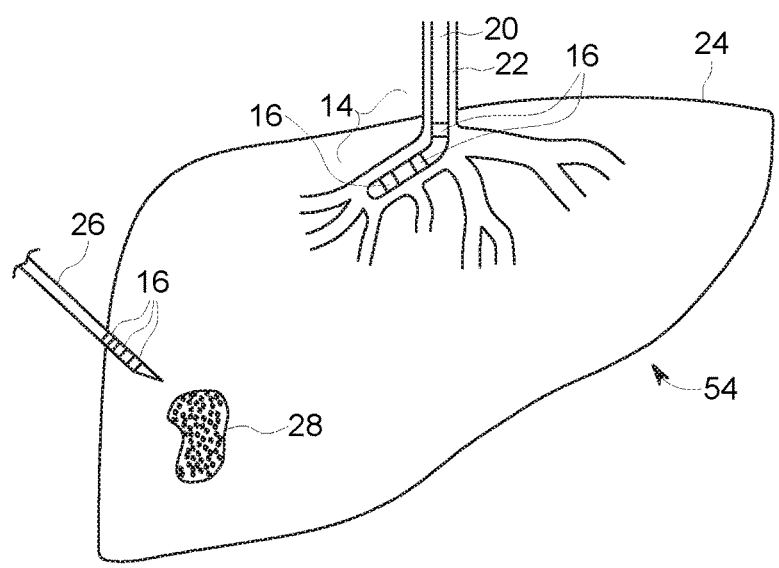
FIG. 2 depicts an interventional device inserted into an organ, in accordance with an embodiment of the present technique.

For example, in an embodiment, the interventional device 10 is a catheter 20. An example of such a catheter 20 might be a 7-french straight catheter suitable for introduction via a jugular or femoral vein and for insertion of the tip, here depicted as reference portion 14, into the hepatic (or other) vasculature, as depicted in FIG. 2. In such an embodiment, the catheter tip may be guided to the hepatic vein 22 (or other vein) under fluoroscopy after introduction of a suitable contrast agent to the blood stream. Once at the liver 24, the tip of the catheter 20 can be lodged into the hepatic vein 22 such that the reference portion 14 is deep within the liver 24 and in a stable position. In such an implementation, because the liver 24 moves essentially as a rigid body during respiration and because the reference portion 14 is lodged within the hepatic vein 22, the reference portion 14 will move with the liver 24. Because the reference portion 14 will move with the liver 24, the reference portion 14 can act as a dynamic reference with regard to the liver 24. As a result, an interventional procedure, such as insertion of a biopsy needle 26 into a structure of interest 28 (e.g., a lesion), can be performed using image-guided techniques using position or motion information obtained using the sensor elements 16 integrated on the reference portion 14. Moreover, to further facilitate the interventional procedure, the biopsy needle 26, or other interventional tool, may include the sensor elements 16 to provide position or motion information regarding the position and/or orientation of the biopsy needle (or other tool).

In certain implementations, the sensor elements 16 are not provided in a linear arrangement, i.e., the sensor elements 16 do not form a single line, such that the respective sensor elements 16 can be distinguished from one another based upon their known spatial relationships. For example, in the depicted embodiments of FIGS. 1 and 2, the sensor elements 16 are provided on a curved portion of the catheter 20 such that the information received from the sensor elements 16 can be used to distinguish the respective sensor elements 16 from one another based on known spatial and/or geometric relationship of the sensor elements 16 to one another.

In one embodiment, the sensor elements 16 are provided as electromagnetic (EM) microsensors, such as solid or hollow EM coils, that are integrated into or securely attached to the interventional device 10. In implementations employing such EM coils, each EM sensor coil can provide information regarding the orientation of the respective coil in two directions. In one embodiment, however, a single coil cannot provide sufficient information to determine the roll of the respective coil since the coils are axisymmetric. Therefore, each coil, in such an embodiment, has five degrees of freedom. If at least two such coils are combined into or integrated onto a device, such as the interventional device 10, so that the coils have a known and fixed relationship to one another, then six degrees of freedom (x, y, z, roll, pitch, yaw) can be determined from the aggregate or combined information obtained form the two or more coils. In this way, the EM fields generated by the EM coils may be used to determine the position and orientation of the portion of the interventional device upon which they are integrated. For example, in the embodiment depicted in FIGS. 1 and 2, the sensor elements 16 (which are presumed to be EM coils in this example) that are fixed on the reference portion 14 of the catheter 20 allow the position and orientation of the reference portion 14 of the catheter 20 to be determined based upon the EM fields generated by the EM coils.

Figure 3:
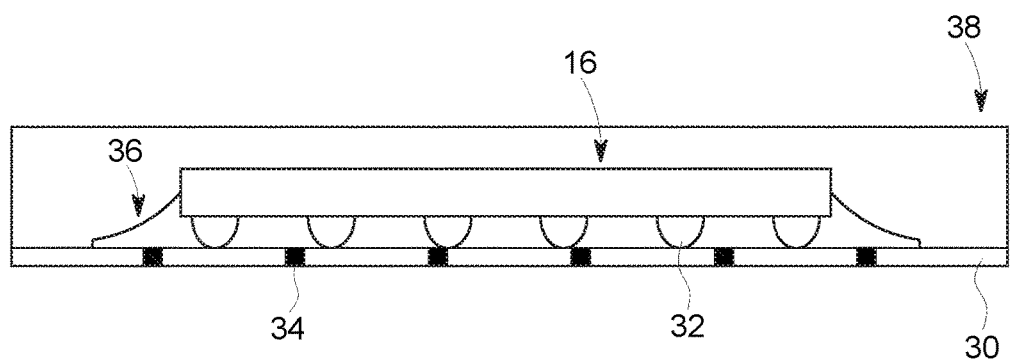
FIG. 3 depicts a magnetoresistance sensor placed on a substrate, in accordance with an embodiment of the present technique.

In another embodiment, the sensor elements 16 are provided as magnetoresistance (MR) sensors 16, as illustrated in FIG. 3. In such an embodiment, the magnetoresistance sensor 16 provides a change in electrical resistance of a conductor or semiconductor when an external magnetic field is applied. Additionally, each individual magnetoresistance sensor 16 may be suitable for providing position information (i.e., x, y, and z position data) and/or orientation information (i.e., roll, pitch, and yaw orientation data) in the presence of an external magnetic field. Thus, the magnetoresistance sensor 16 operates with six degrees of freedom.[]

In certain embodiments, the magnetoresistance sensor 16 may include an area array or peripheral array interconnect flip chip magnetoresistance sensor 16. The flip chip structure of the magnetoresistance sensor 16 is coupled to a flexible or rigid substrate 30 (e.g. printed circuit board (PCB)) as well as connectors to external circuitry. The substrate 30 may be suitable to be affixed to or within the interventional device 10 and/or surgical tool (e.g., the biopsy needle 26). The electrical connection may be provided on or in communication with pads of the magnetoresistance sensor 16 and corresponding pads on the substrate 30. The substrate 30 may include or be connected to one or more wires, traces, flex-circuits, or other conductive structures 34 that allow data to be read out from the magnetoresistance sensor 16. The magnetoresistance sensor 16 may also include an underfill material 36 (e.g., an epoxy) that may be applied to the magnetoresistance sensor 16 to fill some or all of the open space between the magnetoresistance sensor 16 and the substrate 30, thereby providing additional thermomechanical stability. Further, a mold cap 38 or other covering or protective layer may be deposited or coated on the magnetoresistance sensor 16 to provide additional protection and/or stability.

As described above, an interventional device 10, whether equipped with electromagnetic coils or magnetoresistance sensors, may be used accordance with the present technique to allow image-guided invasive procedures. As will be appreciated, any imaging modality suitable for use in an image-guided interventional procedure may be employed in the present technique. Examples of such imaging modalities include X-ray based imaging techniques which utilize the differential attenuation of X-rays to generate images (such as three-dimensional fluoroscopy, computed tomography (CT), tomosynthesis techniques, and other X-ray based imaging technologies). Other exemplary imaging modalities suitable for image-guided interventional procedures may include magnetic resonance imaging (MRI), ultrasound or thermoacoustic imaging techniques, and/or optical imaging techniques Likewise, nuclear medicine imaging techniques (such as positron emission tomography (PET) or single positron emission computed tomography (SPECT)) that utilize radiopharmaceuticals may also be suitable imaging technologies for performing image-guided interventional procedures. Likewise, combined imaging modality systems, such as PET/CT systems, may also be suitable for performing image-guided interventional procedures as described herein. Therefore, throughout the present discussion, it should be borne in mind that the present techniques are generally independent of the system or modality used to acquire the image data. That is, the technique may operate on stored raw, processed or partially processed image data from any suitable source.

Figure 4:
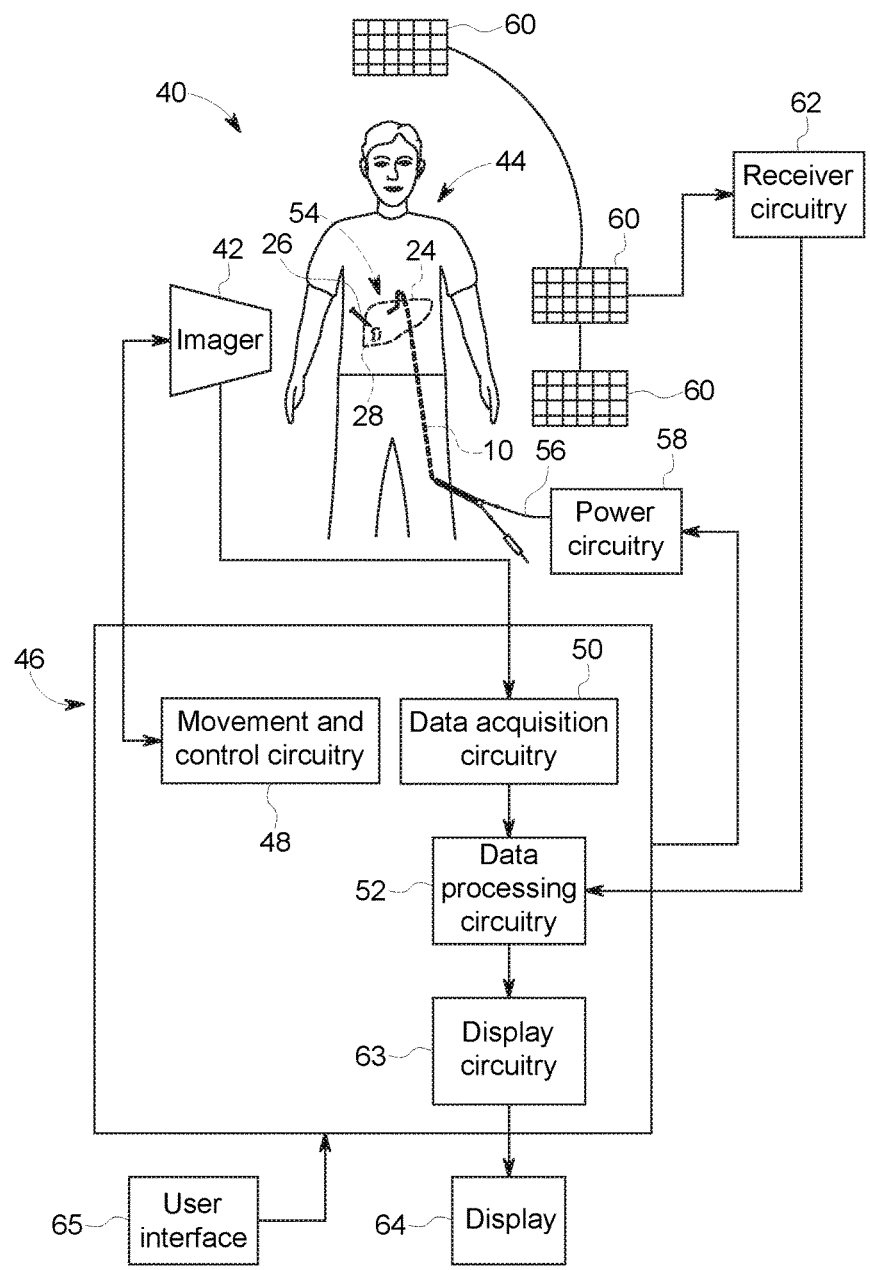
FIG. 4 depicts components of an imaging system and a position determining system, in accordance with one embodiment of the present technique.

For example, turning now to FIG. 4, an overview of an exemplary generalized imaging system 40, which may be representative of various imaging modalities, is depicted. The generalized imaging system 40 typically includes some type of imager 42 which detects signals and converts the signals to useful data. As described more fully below, the imager 42 may operate in accordance with various physical principles for creating the image data. In general, however, image data indicative of regions of interest in a patient 44 are created by the imager 42 in a digital medium for use in image-guided interventional procedures.

The imager 42 may be operated by system control circuitry 46 which controls various aspects of the imager operation and acquisition and processing of the image data as well as dynamic reference data acquired using the present techniques. In the depicted generalized embodiment, the system control circuitry 46 includes movement and control circuitry 48 useful in operating the imager 42. For example, the movement and control circuitry 48 may include radiation source control circuits, timing circuits, circuits for coordinating the relative motion of the imager 42 (such as with regard to a patient support and/or detector assembly), and so forth. The imager 42, following acquisition of the image data or signals, may process the signals, such as for conversion to digital values, and forwards the image data to data acquisition circuitry 50. For digital systems, the data acquisition circuitry 50 may perform a wide range of initial processing functions, such as adjustment of digital dynamic ranges, smoothing or sharpening of data, as well as compiling of data streams and files, where desired. The data are then transferred to data processing circuitry 52 where additional processing and analysis are performed. For the various digital imaging systems available, the data processing circuitry 52 may perform substantial reconstruction and/or analyses of data, ordering of data, sharpening, smoothing, feature recognition, and so forth.

In addition to processing the image data, the processing circuitry 52 may also receive and process motion or location information related to an anatomical region of interest, such as the depicted internal organ 54 and/or lesion 28. In the depicted embodiment, an interventional device 10 is placed on or near the internal organ 54 (here depicted as the liver 24 of the patient 44). The interventional device 10 and/or the surgical tool 26, as discussed above, may each be provided with various (for example, one or more) sensor elements 16 (see FIGS. 1 and 2) configured to provide position information. In one embodiment, the sensor elements 16 are EM coils each configured to generate a distinctive and distinguishable EM field. In other embodiments, the sensor elements 16 are one or more magnetoresistance sensors that generate position and/or orientation data in response to an external magnetic field. In certain embodiments where the sensor elements 16 are powered, the sensor elements 16 may be connected, such as via one or more conductive wires 56 running through the catheter, to suitable power circuitry 58, such as an electrical power source or outlet or a suitable battery. While in the depicted embodiment the power circuitry 58 is depicted as being separate from the system control circuitry 46, in other embodiments the power circuitry 58 may be part of the system control circuitry 46.

In the depicted embodiment, the signals or fields generated by the sensor elements 16 are detected by one or more antennas 60. The detected location information is provided to or acquired by receiver circuitry 62 which in turn provides the location data to the processing circuitry 46. As discussed in greater detail below, the location data may be used in conjunction with the image data to facilitate an image-guided procedure.

The processed image data and/or location data may be forward to display circuitry 63 for display at a monitor 64 for viewing and analysis. While operations may be performed on the image data prior to viewing, the monitor 64 is at some point useful for viewing reconstructed images derived from the image data collected. The images may also be stored in short or long-term storage devices which may be local to the imaging system 40, such as within the system control circuitry 46, or remote from the imaging system 40, such as in picture archiving communication systems. The image data can also be transferred to remote locations, such as via a network.

For simplicity, certain of the circuitry discussed above, such as the movement and control circuitry 48, the data acquisition circuitry 50, the processing circuitry 46, and the display circuitry 63, are depicted and discussed as being part of the system control circuitry 46. Such a depiction and discussion is for the purpose of illustration only, however, and is intended to merely exemplify one possible arrangement of this circuitry in a manner that is readily understandable. In other embodiments the depicted circuitry may be provided in different arrangements and/or locations. For example, certain circuits may be provided in different processor-based systems or workstations or as integral to different structures, such as imaging workstations, system control panels, and so forth, which functionally communicate to accomplish the techniques described herein.

The operation of the imaging system 40 may be controlled by an operator via a user interface 65 which may include various user input device, such as a mouse, keyboard, touch screen, and so forth. Such a user interface may be configured to provide inputs and commands to the system control circuitry 46, as depicted. Moreover, it should also be noted that more than a single user interface 65 may be provided. Accordingly, an imaging scanner or station may include an interface which permits regulation of the parameters involved in the image data acquisition procedure, whereas a different user interface may be provided for manipulating, enhancing, and viewing resulting reconstructed images.

Figure 5:
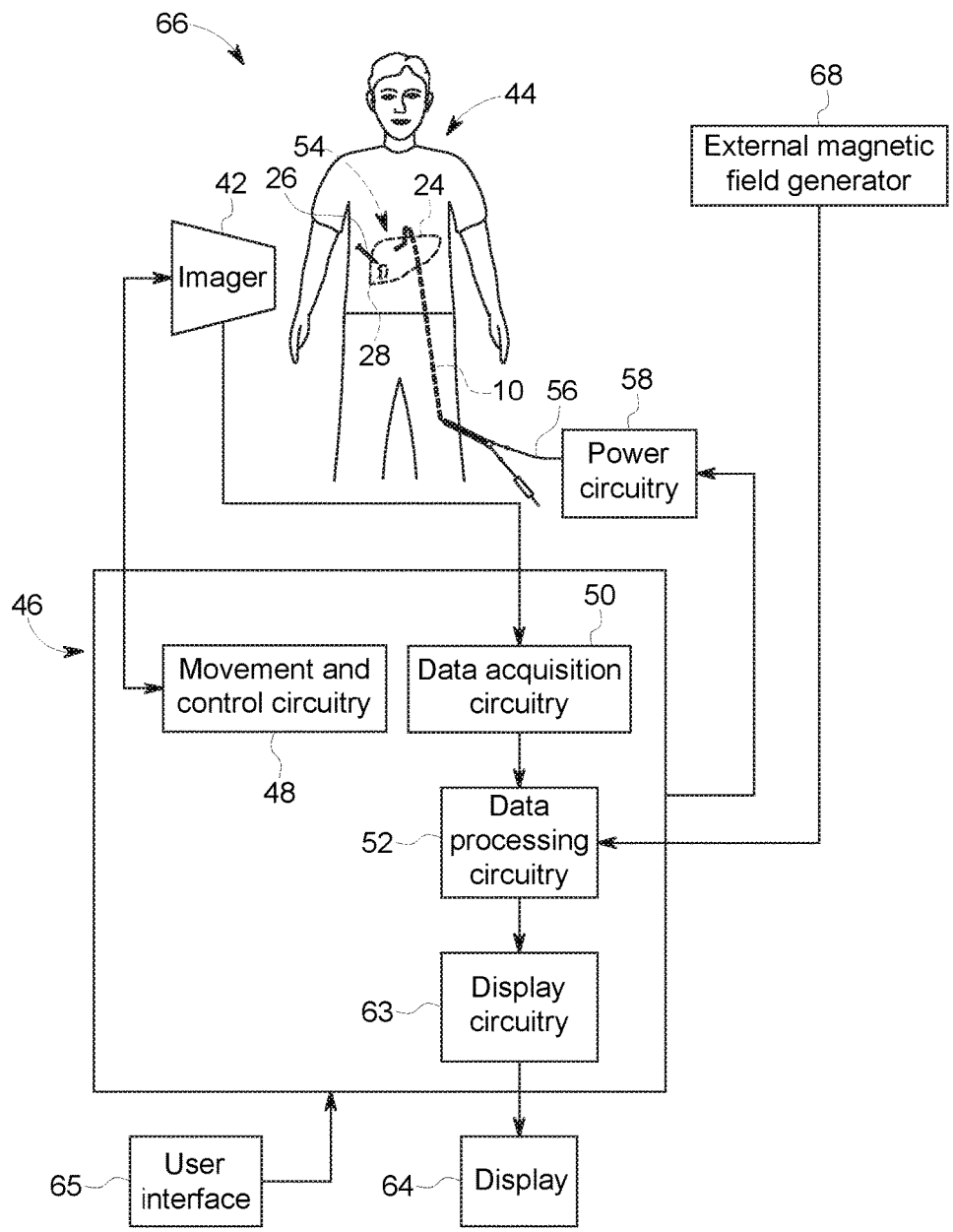
FIG. 5 depicts components of an imaging system and a position determining system, in accordance with a further embodiment of the present technique.

As noted above, the sensor elements 16 may also be provided as magnetoresistance sensors 16. Accordingly, FIG. 5 is an overview of a generalized imaging system 66 that may be used in conjunction with the magnetoresistance sensors 16. The imaging system 66 may include the imager 42, the system control circuitry 46, the power circuitry 58, the monitor 64, and the user interface 65 as described above with respect to FIG. 4. However, rather than the antennas 60 and the receiver circuitry 62, the imaging system 66 includes an external magnetic field generator 68 (e.g., electromagnetic transmitter). The external magnetic field generator 68 may generate an alternating current (AC) or pulsed direct current (DC) magnetic field. The magnetoresistance sensors 16 generate signals representative of location data (including position and/or orientation data) in response to the applied magnetic field, which may be sent via the wires 56 to the system control circuitry 46 (in particular the data processing circuitry 52). As discussed in more detail below, the location data may be used in conjunction with the image data to facilitate an image-guided procedure. The processed image data and/or location data may be forward to display circuitry 63 for display at the monitor 64 for viewing and analysis.

Figure 6:
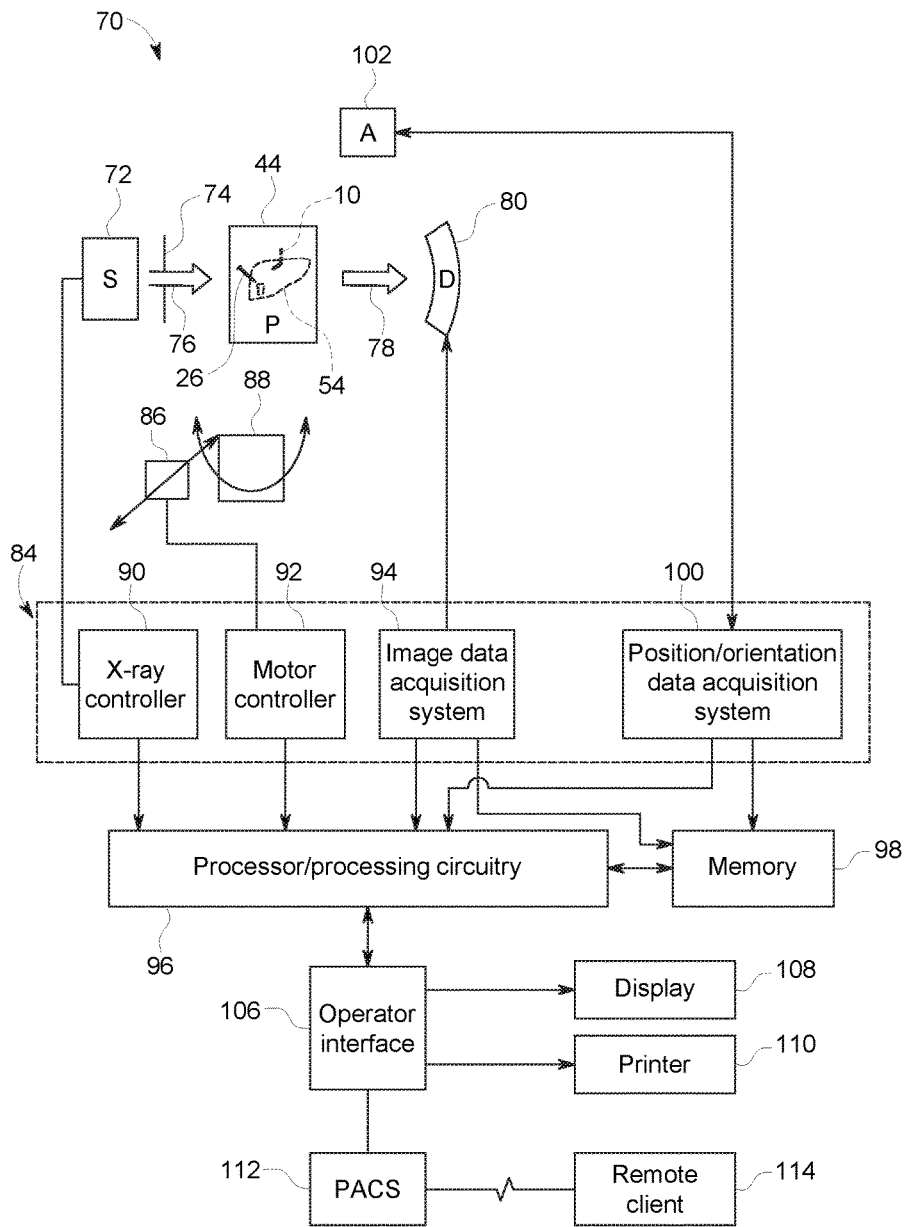
FIG. 6 depicts components of a computed tomography or three-dimensional fluoroscopy imaging system and a position determining system, in accordance with an embodiment of the present technique.

To discuss the technique in greater detail, a specific medical imaging modality based generally upon the overall system architecture outlined in FIG. 4 is depicted in FIG. 6, which generally represents an X-ray based system 70. It should be noted that, while reference is made in FIG. 6 to an X-ray based system, the present technique also encompasses other imaging modalities, as discussed above, such as MRI, PET, SPECT, ultrasound, and so forth.

In the depicted exemplary embodiment, FIG. 6 illustrates diagrammatically an X-ray based imaging system 70 for acquiring and processing image data. In the illustrated embodiment, imaging system 70 is a computed tomography (CT) system or three-dimensional fluoroscopy imaging system designed to acquire X-ray projection data, to reconstruct the projection data into a two or three-dimensional image, and to process the image for display and analysis in accordance with the present technique. In the embodiment illustrated in FIG. 6, X-ray based imaging system 70 includes a source of X-ray radiation 72 positioned adjacent to a collimator 74. The X-ray source 72 may be a standard X-ray tube or one or more solid-sate X-ray emitters.

In the depicted embodiment, the collimator 74 permits a stream of radiation 76 to pass into a region in which a subject, such as the patient 44 is positioned. The stream of radiation 76 may be generally fan or cone shaped, depending on the configuration of the detector array as well as the desired method of data acquisition. A portion of the radiation 78 passes through or around the patient 44 and impacts a detector array, represented generally as reference numeral 80. Detector elements of the array produce electrical signals that represent the intensity of the incident X-ray beam. The signals generated by the detector array 80 may be subsequently processed to reconstruct a visual representation (i.e., an image or volumetric representation) of the features within the patient 44. For example, images of the internal organ 54 may be reconstructed in the depicted embodiment.

A variety of configurations of the detector 80 may be employed in conjunction with the techniques described herein. For example, the detector 80 may be a multi-row detector, such as a detector having eight or sixteen rows of detector elements, which achieves limited longitudinal coverage of the object or patient being scanned. Similarly, the detector 80 may be an area detector, such as a high-resolution radiographic detector having hundreds of rows of detector elements, which allows positioning of the entire object or organ being imaged within the field of view of the system 70. Regardless of the configuration, the detector 80 enables acquisition and/or measurement of the data used in image reconstruction of the internal organ 54.

The source 72 is controlled by a system controller 84, which furnishes both power, and control signals for examination procedures. Moreover, the detector 80 is coupled to the system controller 84, which commands acquisition of the signals generated in the detector 80. The system controller 84 may also execute various signal processing and filtration functions, such as for initial adjustment of dynamic ranges, interleaving of digital image data, and so forth. In general, system controller 84 commands operation of the imaging system 70 to execute examination protocols and to process acquired data. In the present context, system controller 84 also includes signal processing circuitry, typically based upon a general purpose or application-specific digital computer, associated memory circuitry for storing programs and routines executed by the computer (such as programs and routines for implementing the present technique), as well as configuration parameters and image data, interface circuits, and so forth.

In the embodiment illustrated in FIG. 6, the system controller 84 is coupled to a linear positioning subsystem 86 and rotational subsystem 88. The rotational subsystem 88 enables the X-ray source 72, collimator 74 and the detector 80 to be rotated one or multiple turns around the patient 44. It should be noted that the rotational subsystem 88 might include a gantry or C-arm apparatus. Thus, the system controller 84 may be utilized to operate the gantry or C-arm. The linear positioning subsystem 86 typically enables a patient support, such as a table, upon which the patient rests, to be displaced linearly. Thus, the patient table may be linearly moved relative to the gantry or C-arm to generate images of particular areas of the patient 44.

Additionally, the source 72 of radiation may be controlled by an X-ray controller 90 disposed within the system controller 84. Particularly, the X-ray controller 90 may be configured to provide power and timing signals to the X-ray source 72. A motor controller 92 may also be part of the system controller 84 and may be utilized to control the movement of the rotational subsystem 88 and the linear positioning subsystem 86.

Further, the system controller 84 is also illustrated as including an image data acquisition system 94. In this exemplary embodiment, the detector 80 is coupled to the system controller 84, and more particularly to the image data acquisition system 94. The image data acquisition system 94 receives data collected by readout electronics of the detector 80. The image data acquisition system 94 typically receives sampled analog signals from the detector 90 and converts the data to digital signals for subsequent processing by processing circuitry 96, which may, for example, be one or more processors of a general or application specific computer.

As depicted, the system controller 84 also includes a position/orientation data acquisition system 100 configured to acquire position and orientation data from one or more antennas 102. In the depicted embodiment, the one or more antennas 102 detect signals and/or fields generated by sensor elements 16 (e.g., electromagnetic sensors) on an interventional device 10 placed on or in the internal organ 54 undergoing imaging or in the vasculature associated with the internal organ 54. The position/orientation data acquisition system 100 processes signals acquired from the antennas 102 to generate position and/or orientation information about the interventional device 10 which is representative of the internal organ 54 or of vasculature associated with the internal organ 54. The position and/or orientation information generated by the position/orientation data acquisition system 100 may be provided to the processing circuitry 96 and/or a memory 98 for subsequent processing.

The processing circuitry 96 is typically coupled to the system controller 84. The data collected by the image data acquisition system 94 and/or by the position/orientation data acquisition system 100 may be transmitted to the processing circuitry 96 for subsequent processing and visual reconstruction. The processing circuitry 96 may include (or may communicate with) a memory 98 that can store data processed by the processing circuitry 96 or data to be processed by the processing circuitry 96. It should be understood that any type of computer accessible memory device capable of storing the desired amount of data and/or code may be utilized by such an exemplary system 70. Moreover, the memory 98 may include one or more memory devices, such as magnetic or optical devices, of similar or different types, which may be local and/or remote to the system 70. The memory 98 may store data, processing parameters, and/or computer programs having one or more routines for performing the processes described herein.

The processing circuitry 96 may be adapted to control features enabled by the system controller 84, i.e., scanning operations and data acquisition. For example, the processing circuitry 96 may be configured to receive commands and scanning parameters from an operator via an operator interface 106 typically equipped with a keyboard and other input devices (not shown). An operator may thereby control the system 70 via the input devices. A display 108 coupled to the operator interface 106 may be utilized to observe a reconstructed visual representation. Additionally, the reconstructed image may also be printed by a printer 110, which may be coupled to the operator interface 106. As will be appreciated, one or more operator interfaces 106 may be linked to the system 70 for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The processing circuitry 96 may also be coupled to a picture archiving and communications system (PACS) 112. Image data generated or processed by the processing circuitry 96 may be transmitted to and stored at the PACS 112 for subsequent processing or review. It should be noted that PACS 112 might be coupled to a remote client 114, radiology department information system (RIS), hospital information system (HIS) or to an internal or external network, so that others at different locations may gain access to the image data.

Figure 7:
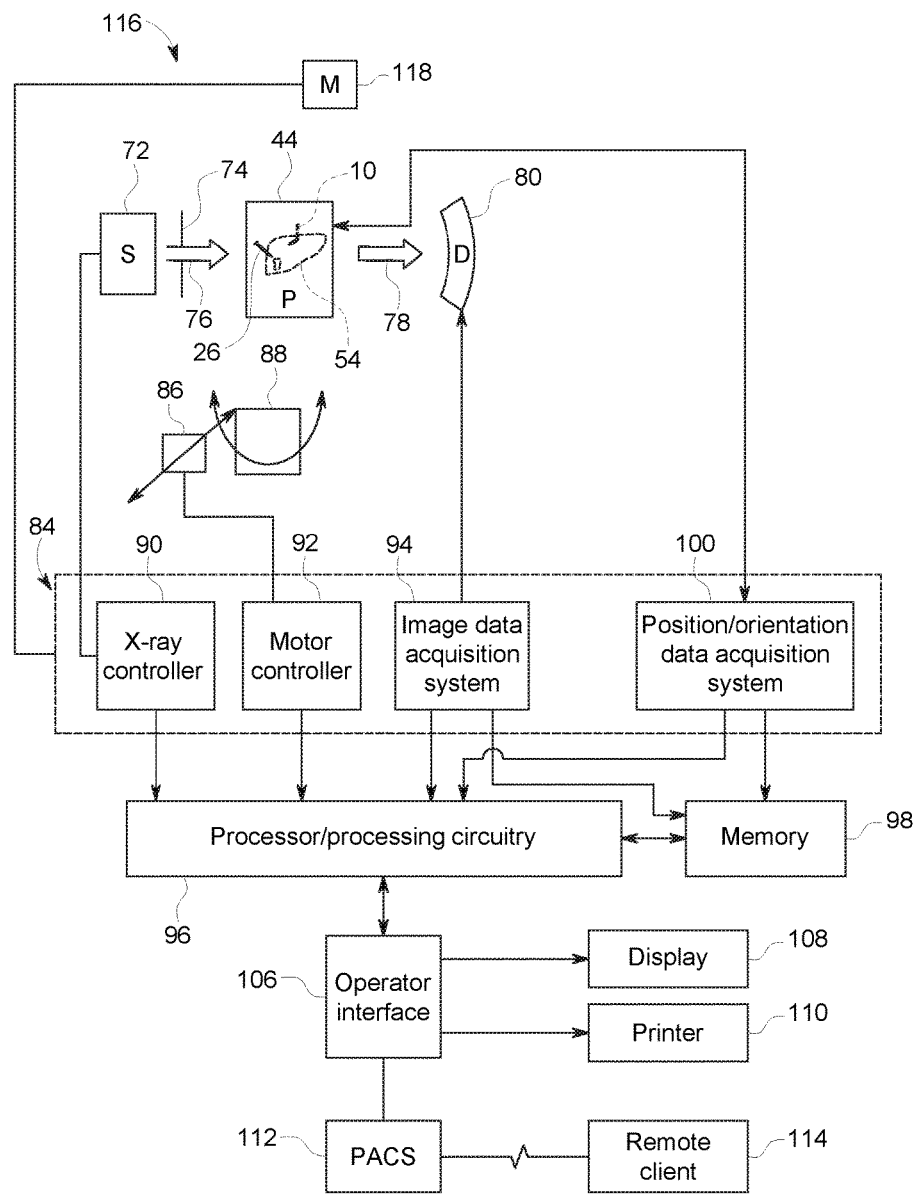
FIG. 7 depicts components of a computed tomography or three-dimensional fluoroscopy imaging system and a position determining system, in accordance with a further embodiment of the present technique.

Additionally, a specific medical imaging modality based generally upon the overall system architecture outlined in FIG. 5 is depicted in FIG. 7, which generally represents an X-ray based imaging system 116. It should be noted that, while reference is made in FIG. 7 to an X-ray based system, the present technique also encompasses other imaging modalities, as discussed above, such as MRI, PET, SPECT, ultrasound, and so forth. The imaging system 116 may generally operate as discussed above with respect to FIG. 6. However, the position/orientation data acquisition system 100 of the imaging system 116 may be configured to acquire position and orientation data from one or more magnetoresistance sensors 16 disposed on or in the interventional device 10 and/or the surgical tool (e.g., biopsy needle 26), when the magnetoresistance sensors 16 are exposed to an applied magnetic field. Accordingly, the imaging system 116 includes an external magnetic field generator 118 (e.g., electromagnetic transmitter), which may be controlled by the system controller 84. The position/orientation data acquisition system 100 processes data acquired from the magnetoresistance sensors 16 to generate position and/or orientation information about the magnetoresistance sensors 14 of the interventional device 10 and/or the biopsy needle 26. The position and/or orientation information generated by the position/orientation data acquisition system 100 may be provided to the processing circuitry 96 and/or a memory 98 for subsequent processing.

The systems and devices described above may be utilized, as described herein, to provide dynamic referencing for a region of a patient undergoing an interventional procedure. In an exemplary embodiment, dynamically acquired position and orientation data for the region of the patient may be acquired using the interventional device 10 and sensor elements 16 and this data may be automatically registered with concurrently or previously acquired image data without the use of anatomical or fiducial markers. In this way, the interventional procedure may be performed or guided based upon the dynamically referenced visual representation.

Figure 8:
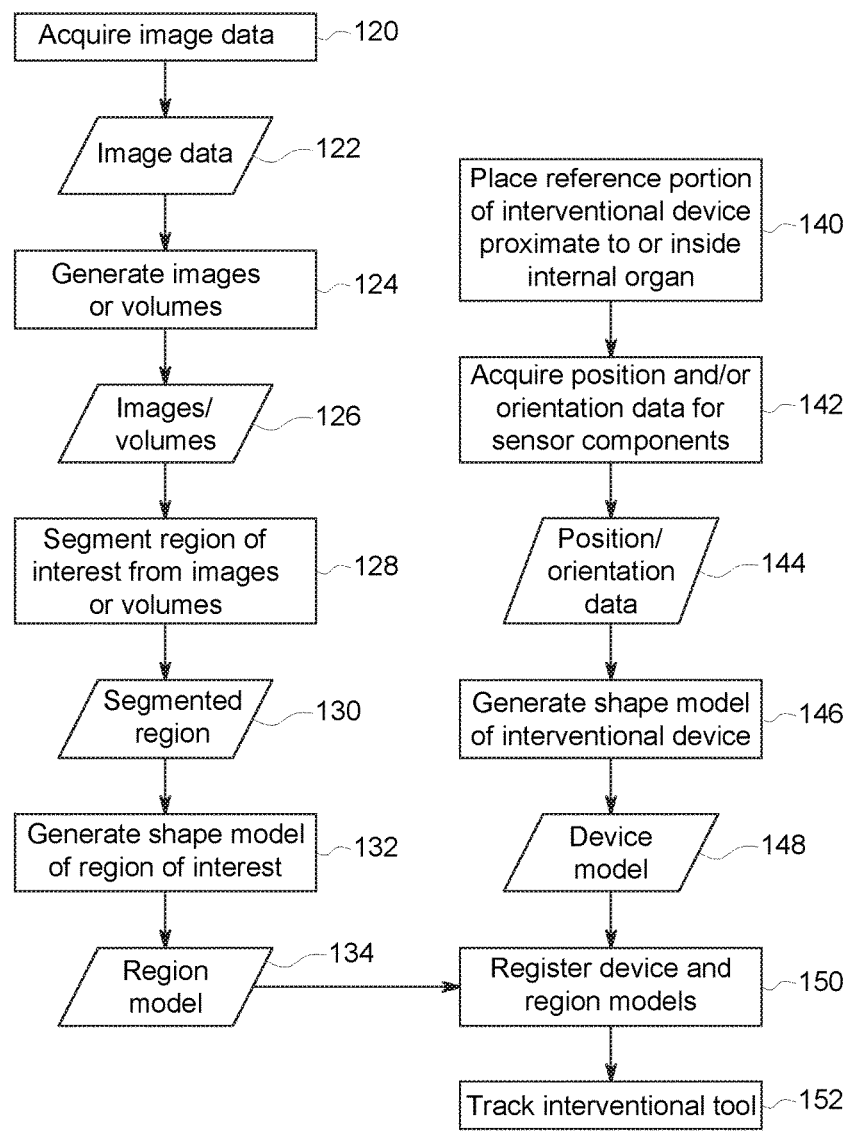
FIG. 8 depicts examples of acts for using a position determining system, in accordance with an embodiment of the present technique.

For example, referring to FIG. 8, examples of acts corresponding to one implementation of the present technique are provided. In the implementation depicted in FIG. 8, the image data 122 is acquired (Block 120) prior to the invasive procedure. As noted above, the image data 122 may be acquired using one or more suitable imaging modalities, such as three-dimensional fluoroscopy, CT, MRI, and so forth. In the depicted embodiment, the image data 122 is used to generate (Block 124) one or more visual representations, such as images or volumes 126, of the internal organ 54 (see FIG. 2) or and/or associated vasculature. In one embodiment, the image data 122 is acquired after introduction of a contrast agent to the patient's bloodstream, thereby providing good contrast for the vasculature in the image data 122.

The images or volumes 126 are segmented (Block 128) in the depicted implementation to provide one or more segmented regions 130. Such a segmentation process typically identifies pixels or those portions of an image representing common structures, such as organs, tissues, vasculature, and so forth. For example, a segmentation a process may identify surfaces or boundaries defining an organ, tissue, or blood vessel (such as by changes in intensity or some other threshold criteria). In this way, all of those pixels representing respective organs, tissues or blood vessels, portions of such organs, tissues or blood vessels, or regions proximate or connected to such organs, tissues, or blood vessels, may be identified and distinguished from one another, allowing processing or evaluation of only the portions of an image associated with the organs, tissues, or blood vessels of interest. For example, in an embodiment where contrast agents are employed and the liver and hepatic vasculature are the region of interest, the hepatic vein can be segmented in the images and/or volumes 126. In this manner, a geometric or spatial model of the segmented hepatic vein can be generated for subsequent procedures, as described below.

The images or volumes 126 may be segmented using known segmentation techniques, such as intensity and/or volume thresholding, connectivity clustering, and so forth. In one embodiment, the segmentation allows the organ, tissue, blood vessel, or other region of interest to be geometrically or spatially modeled, as noted above. In an exemplary embodiment, the segmented region corresponds to the internal organ 54 or blood vessel within which the interventional device 10 (see FIGS. 1 and 2) will be placed for dynamic referencing. While the depicted actions describe an embodiment in which images or volume 126 generated from the acquired image data 122 are segmented, in other embodiments the segmentation may be performed on the image data 122 itself, with the segmented image data being subsequently used to generate images or volume of the internal organ 54, blood vessel, or other region of interest. Based upon the segmented image or volume of the internal organ or blood vessel, i.e., the segmented region 130, a model 134 of the region is generated (Block 132) which generally corresponds to the internal organ 54, blood vessel, or other region of interest as determinable form the imaging process.

In some embodiments, the region model 134 may incorporate image data acquired using more than one type of imaging modality. For example, in some embodiments, it may be desirable to use image data derived form both an MRI system and an X-ray based imaging system, such as a three-dimensional fluoroscopy system. In such an embodiment, the signals acquired by both system may be registered, as discussed below, such that the combined images and/or volumes 126, segmented region 130 and/or region model 134 consists of or is representative of the image information acquired by each imaging modality.

During the invasive procedure performed on the internal organ 54 (or other region of interest), the interventional device 10 is placed (Block 140) in, on, or near the internal organ 54, such as in the vasculature leading to the internal organ 54. As noted above, the interventional device 10 includes at least three sensor elements 16, which in one embodiment, are provided on a reference portion 14 of the interventional device 10. The sensor elements 16 generate respective signals (such as respective EM fields) which may be acquired (Block 142) or measured to derive position and/or orientation data 144 for each respective sensor element 16. The position and/or orientation data 144 may be used to generate (Block 146) a device model 148 representing shape, position and/or orientation of the interventional device 10.

The device model 148 derived from the position and/or orientation data 144 is registered (block 150) with the region model 134 generated using the imaging process. In one embodiment, the registration of the device model 148 and the region model 134 is accomplished automatically, such as using iterative closest point techniques. In this manner, the sensor elements 16 of the interventional device 10 are automatically registered to the images of the region of interest, i.e., the internal organ 54 and/or associated vasculature, thereby allowing the position and/or orientation of the internal organ 54 or associated vasculature to be modified in a visual representation based on the most recent position and/or orientation data from the sensor elements 16 of the interventional device.

An image-guided invasive procedure may be performed using the registered device model 148 (based on the position and/or orientation data) and region model 134 (based on the image data). In particular, once the previously acquired image-based information or model is registered to the measured position and/or orientation data, changes in the position and/or orientation data can be used to visually indicate changes to the image-based model. In other words, a displayed image of the internal organ 54 or the associated vasculature may be updated, modified, altered, or otherwise, changed, based on the most current position and/or orientation data obtained from the sensor elements 16 of the interventional device 10. In this way, even though no imaging processes are occurring during the operation, the previously acquired image data can be updated and manipulated to provide an accurate and current representation of the internal organ and/or associated vasculature undergoing the procedure.

Based on this registration between the region model 134 (derived the image data) and device model 148 (derived from the sensor element data), an interventional tool may be tracked (Block 152) during an interventional procedure. Examples of such interventional tools that may be tracked include biopsy needles, catheters, ablation needles, and so forth. Typically the interventional tool being tracked also includes a sensor element 16, such as an electromagnetic or magnetoresistance sensor, so that position and/or orientation information for the interventional tool is also acquired, thereby allowing the position of the interventional tool to be displayed in conjunction with the registered image of the moving and/or deformed internal organ 54 or the vasculature of such an organ. In this manner, a system such as those described herein, may display to a user in real-time or substantially real-time the location of the interventional device relative to the moving and/or deformed internal organ 54 or its vasculature.

Figure 9:
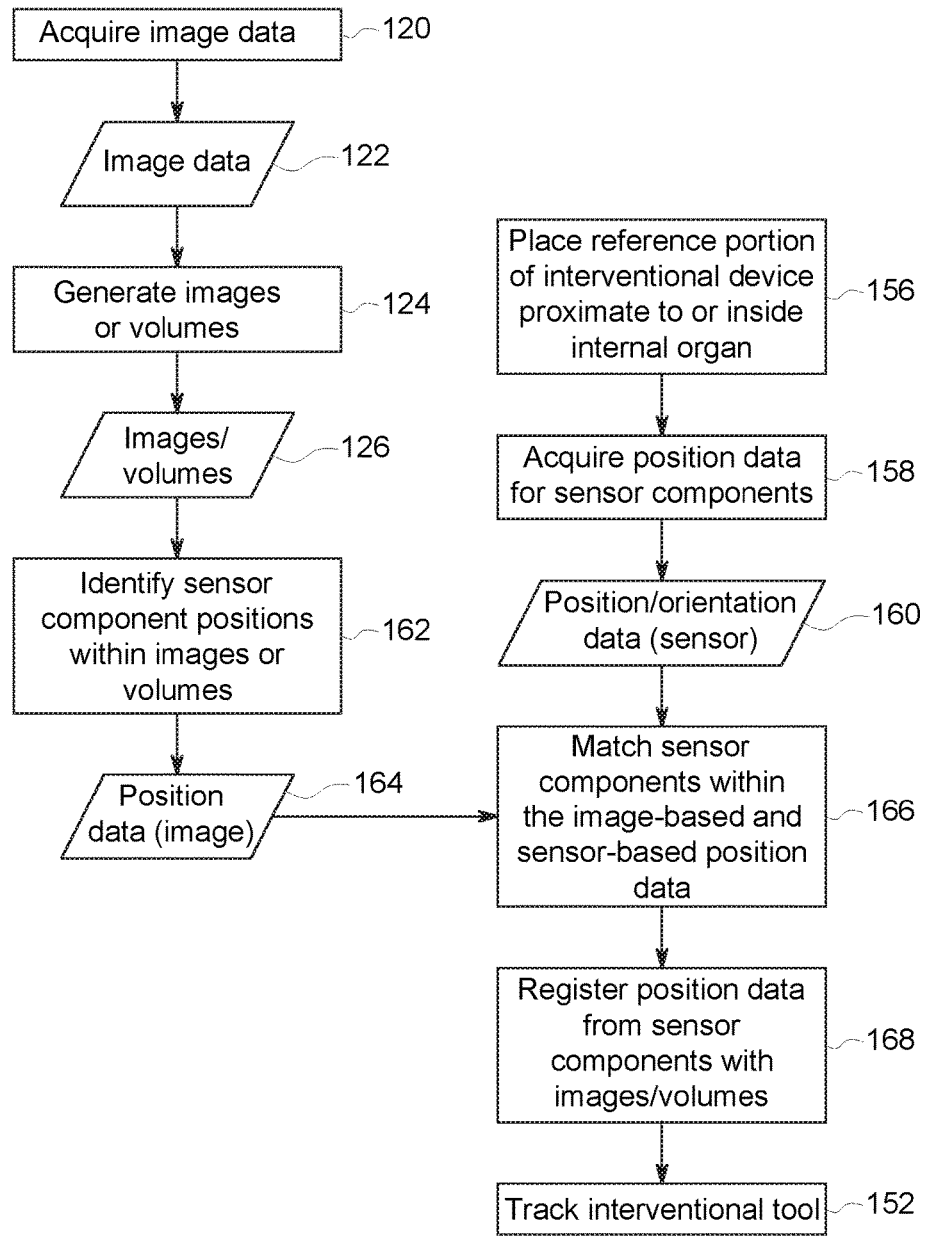
FIG. 9 depicts examples of acts for using a position determining system, in accordance with a further embodiment of the present technique.

While the preceding described an implementation in which the imaging procedure is performed prior to the interventional procedure, in other implementations the imaging procedure is performed concurrently with the interventional procedure. For example, referring to FIG. 9, acts associated with a further exemplary embodiment of the present technique are depicted. In this embodiment, a reference portion 14 of an interventional device 10 is placed (Block 156) in or near an internal organ 54 of interest, such as the vasculature leading to the internal organ 54. Position and/or orientation data 160 is acquired (Block 158) for the sensor elements 16 integrated on the reference portion 14. For example, in embodiments where the sensor elements 16 generate EM signals or fields, these signals or fields can be detected and/or measured, such as using one or more antenna arrays as described above, to derive a position and/or orientation for each respective sensor element 16.

In the depicted embodiment, image data 122 is acquired (Block 120) and is used to generate (Block 124) one or more images and/or volumes 126. Some or all of the sensor elements 16 are located (Block 162) in the images and/or volumes 126 such that the position data 164 for the respective sensor elements 16 is obtained with respect to the images/volumes 126. In an exemplary embodiment, the sensor elements 16 are automatically located in the images/volumes 126. For example, the sensor elements 16 may be automatically located using image processing techniques such as intensity and/or volume thresholding, connectivity clustering, template matching, and so forth. In addition, in some embodiments, the positions of the sensor elements 16 are known with respect to one another based on the measured signals or fields generated by the sensor elements 16. This sensor derived position data 158 may be used to find the sensor elements 16 in the images and/or volumes 126.

Once some or all of the sensor elements 16 are identified in the images and/or volumes, the positions 164 of the sensor elements 16 located in the images and/or volumes may be matched (Block 166) to the corresponding sensor element locations as determined from the sensor position data 160. In other words, the sensor elements 16 located in the images and/or volumes are matched with the corresponding sensor elements signals and/or fields generated by the sensor elements 16. In one embodiment, this may be facilitated by using different sizes of sensor elements 16 on the interventional device 10 such that the sensor elements 16 can be distinguished in the image data and matched to their corresponding sensor signals. Likewise, a priori information about patient position in the images may be used to determine which sensor element 16 is the element and which is the proximal one, thereby allowing matching between the sensor element readings and the identified sensor elements 16 in the images. Alternatively, a sufficiently large number (i.e., four or more) of sensor elements 16 may be provided in one embodiment such that all possible matches may be permuted and the match generating the smallest registration error is selected as the correct match or correspondence.

Based on the established or possible correspondences, the sensor element positions derived using the sensor data and the imaging data are registered (Block 168). As noted above, in some embodiments, the registration and the establishment of the correspondences may actually depend on one another, i.e., the registration errors associated with different possible matches may be used to select the correct correspondence. In one embodiment the centroid of each sensor element 16 as determined in the images and/or volumes is registered to the corresponding sensor element signal in the position data derived from the sensor elements 16. In certain implementations the registration can be accomplished using iterative optimization techniques or a closed form solution. As noted above, in certain embodiments, to obtain a unique registration it is generally desired that the three or more sensor elements not lie on or near a straight line. In certain embodiments, such as in an embodiment where the interventional device 10 is a catheter configured for insertion into the hepatic artery, the interventional device may be designed so that the sensor elements 16 are structurally prevented from being collinear, i.e., the reference portion 14 may be curved. In other embodiments, such as where the sensor elements 16 are not structurally prevented from being collinear, feedback may be provided to the user in the event that a unique registration can not be determined and the user can adjust the position of the interventional device 10 until a unique registration is obtained.

Once the sensor elements 16 are registered in both the sensor space (such as EM space) and the image space, the interventional procedure may be performed using the dynamic tracking of the internal organ based upon the signals from the sensor elements 16. For example, no further imaging may be performed or the image data may be updated only sporadically, with other updates to the images used in the interventional procedure being based upon the continuous, substantially real-time tracking of the sensor elements 16. In this way, even though imaging does not occur or occurs only sporadically during the operation, the displayed images can be updated and manipulated to provide an accurate and current representation of the internal organ 54 (or other internal region) undergoing the procedure.

In one implementation an interventional tool may be tracked (Block 152) during an interventional procedure, using images updated based upon the position data derived form the sensor elements and the registration of these signals with the image and/or volumes 126. Examples of such interventional tools that may be tracked include biopsy needles, catheters, ablation needles, and so forth. Typically the interventional tool being tracked also includes a sensor element 16, such as an EM sensor, so that position and/or orientation information for the interventional tool is also acquired, thereby allowing the position of the interventional tool to be displayed in conjunction with the image updated using the position data for the sensor elements 16. In this manner, a system such as those described herein, may display to a user in real-time or substantially real-time the location of the interventional tool relative to the moving and/or deformed internal organ 54.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A tracking system comprising:
 an interventional tool including a proximal region that remains outside a patient and a terminal region that is suitable for insertion into the patient and placement proximate to or inside an internal organ of the patient, said interventional tool comprising:

a reference portion that is disposed in said terminal region, wherein the reference portion is not physically attached to the internal organ when so placed;

two or more electromagnetic coils integrated on the reference portion of the interventional tool, wherein each of the two or more electromagnetic coils is configured to provide at least position information, wherein each electromagnetic coil of the two or more electromagnetic coils is either sized differently so as to be identifiable in a radiographic image or the two or more electromagnetic coils are positioned so as to be identifiable in the radiographic image based, at least in part, upon their known spatial relationship to one another; and a controller comprising processing circuitry operatively coupled to memory circuitry, wherein the processing circuitry is configured to execute instructions stored on the memory circuitry to cause the processing circuitry to receive the position information generated by the two or more electromagnetic coils and to register the two or more electromagnetic coils to the corresponding position information in the radiographic image of the internal organ based, at least in part, upon either the size differences or known spatial relationship between the two or more electromagnetic coils.

2. The tracking system of claim 1 wherein the interventional device comprises a or a biopsy needle catheter.

3. The tracking system of claim 1 comprising one or more antennas configured to detect electromagnetic fields generated by the two or more electromagnetic coils.

4. The tracking system of claim 1 wherein each electromagnetic coil provides position information in three dimensions and orientation information in two directions.

5. The tracking system of claim 1 comprising at least one imaging modality configured to generate the radiographic image of the internal organ.

6. The tracking system of claim 1 wherein the processing circuitry is configured to execute instructions stored on the memory circuitry to cause the processing circuitry to track the interventional tool using at least the registered position information and the radiographic image of the internal organ.

7. The tracking system of claim 1 wherein the two more electromagnetic coils of the interventional tool are arranged in a non-linear arrangement on a curved portion of the interventional tool.

8. The tracking system of claim 7 comprising one or more antennas configured to detect electromagnetic fields generated by the two or more electromagnetic coils.

9. The tracking system of claim 1 wherein each electromagnetic coil of the two or more electromagnetic coils is sized differently so as to be identifiable in a radiographic image.

10. The tracking system of claim 1 wherein each electromagnetic coil of the two or more electromagnetic coils are positioned so as to be identifiable in the radiographic image based, at least in part, upon their known spatial relationship to one another.

11. A tracking system comprising:

an interventional tool including a proximal region that remains outside a patient and a terminal region that is suitable for insertion into the patient and placement proximate to or inside an internal organ of the patient, said interventional tool comprising:

a reference portion;

two or more electromagnetic coils integrated on the reference portion of the interventional tool, wherein each coil of the two or more electromagnetic coils is configured to provide at least position information, wherein each coil of the two or more electromagnetic coils is either sized differently so as to be identifiable in a radiographic image or the two or more electromagnetic coils are positioned so as to be identifiable in the radiographic image based, at least in part, upon their known spatial relationship to one another; and a controller comprising processing circuitry operatively coupled to memory circuitry, wherein the processing circuitry is configured to execute instructions stored on the memory circuitry to cause the processing circuitry to receive the position information generated by the two or more electromagnetic coils and to register the two or more electromagnetic coils to the corresponding position information in the radiographic image of the internal organ based, at least in part, upon either the size differences or known spatial relationship between the two or more electromagnetic coils.

* * * * *